(12) United States Patent
Kobayashi et al.

(10) Patent No.: US 7,470,646 B2
(45) Date of Patent: Dec. 30, 2008

(54) POLYMER INCARCERATED LEWIS ACID METAL CATALYST

(75) Inventors: Shu Kobayashi, Tokyo (JP); Ryo Akiyama, Tokyo (JP); Nobuyuki Kawai, Tokyo (JP); Masahiro Takeuchi, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 90 days.

(21) Appl. No.: 10/591,829

(22) PCT Filed: Mar. 8, 2005

(86) PCT No.: PCT/JP2005/003949

§ 371 (c)(1),
(2), (4) Date: Sep. 6, 2006

(87) PCT Pub. No.: WO2005/084802

PCT Pub. Date: Sep. 15, 2005

(65) Prior Publication Data

US 2007/0191624 A1    Aug. 16, 2007

(30) Foreign Application Priority Data

Mar. 9, 2004    (JP) .............................. 2004-065250

(51) Int. Cl.
*B01J 31/00* (2006.01)
(52) U.S. Cl. ................ 502/150; 502/159; 502/172; 502/173
(58) Field of Classification Search ............... 502/150, 502/159, 172, 173; 558/332; 564/472
See application file for complete search history.

(56) References Cited

U.S. PATENT DOCUMENTS 6,018,017 A * 1/2000 Le-Khac ................ 528/421
6,352,954 B1 * 3/2002 Kobayashi ............... 502/159
6,429,281 B1 * 8/2002 Dershem et al. ........... 528/412
2003/0119663 A1 * 6/2003 Ooms et al. .............. 502/159

OTHER PUBLICATIONS

Akiyama et al. The Polymer Incarcerated Method for the Preparation of Highly Active Heterogeneous Palladium Catalysts. J Am Chem Soc. Mar. 4, 2003 (published on Web). 125, 3412-3413.*

* cited by examiner

*Primary Examiner*—Jerry Lorengo
*Assistant Examiner*—Noah S Wiese
(74) *Attorney, Agent, or Firm*—Gary C Cohn PLLC

(57) ABSTRACT

The objective is to incarcerate a Lewis acid metal in a polymer and to make this catalyst recoverable while maintaining its function as a Lewis acid metal catalyst. The present invention is a polymer-incarcerated Lewis acid metal catalyst in which a Lewis acid metal is incarcerated in a crosslinked polymer and the crosslinked polymer is crosslinked using the crosslinking groups contained in a crosslinkable polymer. The polymer incarcerated Lewis acid metal catalyst is characterized by the crosslinkable polymer containing at least one type of monomer unit containing hydrophobic substituents and hydrophilic substituents containing crosslinking groups, and the hydrophobic substituents contain aromatic substituents. This crosslinkable polymer preferably comprises at least one type of monomer unit containing hydrophobic substituents and hydrophilic substituents containing crosslinking groups and a monomer unit containing hydrophobic substituents. This catalyst can be obtained by subjecting a polymer micelle incarcerated Lewis acid metal obtained by mixing an organic solution containing a crosslinkable polymer and a Lewis acid metal with a bad solvent to a crosslinking reaction. This catalyst is useful as a catalyst in aldol reactions, cyanolation reactions, allylation reactions, Michael reactions, Mannich reactions, Diels Alder reactions and Friedel Crafts reactions.

19 Claims, No Drawings

POLYMER INCARCERATED LEWIS ACID METAL CATALYST

FIELD OF THE INVENTION

The present invention relates to a catalyst wherein a Lewis acid metal catalyst such as scandium, copper and the like is stabilized in an amphipathic polymer and is immobilized on a carrier or linked to a network with retaining the functions of a Lewis acid metal catalyst and have a recoverable form.

PRIOR ART

Attempts to use a composite material of a metal and a polymer with the properties of each component as a catalyst by immobilizing a variety of metals on many carriers have been made for many years. However, many of the attempts utilized ligand links of nitrogen or phosphorus atoms and generally encountered problems of inadequate catalytic activities and a gradual decline in the activity due to metal leaching upon recovery and recycling.

In addition, a method to immobilize metal clusters on a carrier surface was also developed, but the problems included a catalytic activity that was largely dependent on the cluster size and declined with increasing cluster size.

A report on a catalyst obtained by stabilizing micro metal clusters using a polymer micelle was recently published. However, such metal-polymer micelle composite materials are available as colloidal solutions and are difficult to recover and recycle (Reference 1 and Japanese Patent Application No.2002-267798.).

Metal immobilization methods utilizing microencapsulation methods were recently developed making recovery and recycling possible in various reactions, but the carrier was restricted to organic polymers. In addition, the catalytic activity was not always sufficiently satisfactory (Reference 2).

Reference 1: Japanese Patent Application Public Disclosure (Kokai) No. 2002-66330.
Reference 2: Japanese Patent Application Public Disclosure (Kokai) No. 2002-253972.
Reference 3: S. Kobayashi and S. Nagayama, J. Am. Chem. Soc., 120, 2985-2986 (1998).
Reference 4: S. Kobayashi and R. Akiyama, Angew. Chem., Int. Ed., 41, 2602-2604 (2002).

Problems to be Solved by the Invention

The inventors have already prepared a cluster catalyst that incarcerated metal clusters in a polymer containing hydrophobic substituents (References 3 and 4 and the like). Such a catalyst was difficult to immobilize on a suitable carrier and/or to form masses and it was extremely difficult to recover after using.

Therefore, the objective of the present invention is to make recovery of a catalyst possible by incarcerating a Lewis acid metal in a polymer to immobilize it on a carrier or to link it to a network while maintaining the functions of a Lewis acid metal catalyst.

Means to Solve the Problems

The inventors discovered that the above mentioned problems could be solved by modifying the polymer used in the cluster catalyst, which had been developed by the present inventors (References 3 and 4), to contain aromatic substituents and hydrophilic yet crosslinkable substituents on the side chains, and completed the present invention. This type of polymer constitution enables the hydrophilic sections to incorporate a metal inside and yet for micelles to form in the liquid phase due to the affinity of the hydrophobic substituents toward non-polar solvents. As a result, the metal is incarcerated securely in the polymer through the interaction with the aromatic rings of the polymer and can realize an excellent catalytic activity. Simultaneously, these micelles can be allowed to react with a carrier or can be allowed to react among themselves due to the presence of crosslinking groups. As a result, this Lewis acid metal catalyst can be immobilized on a carrier or the Lewis acid metal catalyst in the form of micelles and can contain numerous three dimensional entanglements. The presence of such a form makes catalyst recovery easy and recycling possible. In addition, a functional membrane in which a Lewis acid metal is dispersed and the like can also be manufactured by molding a film.

That is, the present invention is a polymer incarcerated Lewis acid metal catalyst comprising a Lewis acid metal and a crosslinked polymer, wherein the Lewis acid metal is incarcerated in the crosslinked polymer, the crosslinked polymer is obtained by crosslinking crosslinking groups contained in a crosslinkable polymer, the crosslinkable polymer contains at least one type of monomer unit having a hydrophobic substituent and a hydrophilic substituent having the crosslinking group, and the hydrophobic substituent contains an aromatic substituent.

This crosslinkable polymer preferably comprises at least one type of monomer unit containing a hydrophobic substituent and a hydrophilic substituent containing a crosslinking group and a monomer unit containing a hydrophobic substituent.

In addition, this crosslinkable polymer preferably comprises a monomer unit containing a hydrophilic substituent containing an epoxy group and a monomer unit containing a hydrophilic substituent containing a group that reacts with an epoxy group.

Furthermore, the present invention is the use of the catalyst for aldol reactions, cyanodation reactions, allylation reactions, Michael reactions, Mannich reactions, Diels Alder reactions or Friedel Craft reactions.

EFFECT OF THE INEVNTION

The inventors succeeded in developing a readily recovered and recycled metal-containing polymer micelle catalyst by aggregating a micelle and subsequently crosslinking it after incarcerating a Lewis acid metal in a polymer micelle containing crosslinking groups. In addition, the inventors succeeded in immobilizing a metal on a carrier such as glass, silica gel and the like that was previously accomplished only with difficulties by immobilizing this Lewis acid-containing polymer micelle on a variety of carriers. Now, the metal-containing polymer micelle exhibited very good activity since the Lewis acid metal incarcerated is stabilized inside a micelle.

DETAILED DESCRIPTION OF THE INVENTION

The Lewis acid metal of the present invention is preferably represented by $MY_n$.

M represents Cu (divalent), Zn (divalent), Fe (di or trivalent), Sc (trivalent) or lanthanoid elements ($^{57}$La to $^{71}$Lu) (trivalent), and Cs and Cu are preferred.

n is an integer corresponding to the atomic valance of M and is 2 or 3.

Y represents a halogen atom, OAc, OCOCF$_3$, ClO$_4$, SbF$_6$, PF$_6$ or OSO$_2$CF$_3$(OTf), and OTf is preferred.

The Lewis acid metal catalyst is in a form in which a metal is incarcerated in a polymer micelle through an interaction between the metal and the polymer.

An appropriate well known method may be used to incarcerate the Lewis acid metal in a polymer, but a preferred method is to form a complex (a precursor) of this metal ion with a suitable ligand and to incarcerate the metal in a crosslinkable polymer using the interaction with the hydrophilic substituents the crosslinkable polymer contains.

This crosslinkable polymer contains at least one type of monomer unit containing hydrophobic substituents and hydrophilic substituents containing crosslinking groups, and these hydrophobic substituents contain aromatic substituents. These substituents are linked directly to the crosslinkable polymer main chain, and the crosslinkable polymer may contain multiple types of these substituents. The crosslinked polymer of the present invention is formed by crosslinking the crosslinking groups present in this crosslinkable polymer.

These hydrophobic substituents are aromatic substituents or alkyl groups. These hydrophobic substituents may further contain substituents, but the absence of hydrophilic substituents and crosslinking groups is preferred.

As the alkyl groups, alkyl groups containing less than twenty carbon atoms are preferred.

The aromatic substituents include aryl groups and aralkyl groups.

As the aryl groups, those containing 6 to 10 carbon atoms are ordinarily cited, and those containing 6 carbon atoms are preferred. More specifically, phenyl groups, naphthyl groups and the like, for example, are cited.

As the aralkyl groups, those containing 7 to 12 carbon atoms are ordinarily cited, and those containing 7 to 10 carbon atoms are preferred. More specifically, benzyl groups, phenyl ethyl groups, phenyl propyl groups, phenyl butyl groups, phenyl pentyl groups, phenyl hexyl groups and the like, for example, may be cited.

The aromatic rings in the aryl and aralkyl groups may also contain hydrophobic substituents such as alkyl groups, aryl groups, aralkyl groups and the like. The presence of hydrophilic substituents and reactive groups is not preferred.

The alkyl groups may be linear or branched, and those containing 1 to 4 carbon atoms are ordinarily cited. More specifically, methyl groups, ethyl groups, n-propyl groups, isopropyl groups, n-butyl groups, isobutyl groups, sec-butyl groups, tert-butyl groups and the like, for example, may be cited.

One to five of these substituents ordinarily may be present in the aromatic rings of the aryl and aralkyl groups, but the presence of one to two substituents is preferred.

The crosslinkable hydrophilic substituents may comprise only crosslinking groups or may contain crosslinking groups on a hydrophilic main chain, but crosslinking groups attached to hydrophilic main chains are preferred.

As the crosslinking groups, epoxy groups, carboxyl groups, isocyanate groups, thio isocyanate groups, hydroxyl groups, primary or secondary amino groups and thiol groups may be cited, but these crosslinking groups are preferably epoxy groups, carboxyl groups and isocyanate groups, more preferably epoxy groups and carboxyl groups, and epoxy groups are most preferred. They may also be protected by suitable groups.

In addition, when the crosslinking groups are epoxy groups, carboxyl groups, isocyanate groups or thio isocyanate groups a polymer may further contain hydroxyl groups, primary or secondary amino groups and thiol groups, preferably hydroxyl groups or primary or secondary amino groups and more preferably hydroxyl groups.

As preferred combinations of the crosslinking groups contained in a polymer, epoxy groups alone, epoxy groups and hydroxyl groups, epoxy groups and amino groups, epoxy groups and carboxyl groups, isocyanate groups or thio isocyanate groups alone, isocyanate groups and hydroxyl groups, isocyanate groups and amino groups, isocyanate groups and carboxyl groups, carboxyl groups alone, hydroxyl groups alone, hydroxyl groups and carboxyl groups, carboxyl groups and amino groups and the like may be cited. Of these, epoxy groups alone and the combination of epoxy groups and hydroxyl groups are preferred.

The crosslinking groups may be present on the same hydrophilic side chain or different hydrophilic side chains when a polymer contains multiple types of crosslinking groups, but the presence on different hydrophilic side chains is preferred.

Of these, the presence of hydrophilic substituents containing epoxy groups and hydrophilic substituents containing groups that react with epoxy groups as crosslinking groups is preferred. This group that reacts with epoxy groups may be at least one selected from a group comprising hydroxyl groups, amino groups, thiol groups and carboxyl groups, and hydroxyl groups are preferred.

As the crosslinking group main chain, alkylene groups having 1 to 6 carbon atoms, $-(CH_2)_n(OCH_2CHR^5)_m-$, $-(CH_2)_n(OCH_2C=O)_m-$ or $-(CH_2)_n(COCH_2)_m-$, wherein $R^5$ represents a hydrogen atom or a methyl group and n and m each independently represents integers 1 to 10, is preferred.

On the other hand, a crosslinkable polymer may be any polymer containing these substituents, but those obtained by allowing a monomer containing these substituents to polymerize are preferred.

That is, those with a structure comprising monomer units containing aromatic substituents and hydrophilic substituents containing crosslinking groups, monomer units containing hydrophobic substituents other than aromatic substituents and hydrophilic substituents containing crosslinking groups and monomer units containing hydrophobic substituents are preferred as the crosslinkable polymer.

As examples of such a crosslinkable polymer, the following may be cited.

(1) A crosslinkable polymer comprising monomer units containing aromatic substituents and hydrophilic substituents containing epoxy groups, monomer units containing aromatic substituents and hydrophilic substituents containing groups that react with epoxy groups and monomer units containing hydrophobic substituents.

(2) A crosslinkable polymer comprising monomer units containing aromatic substituents and hydrophilic substituents containing epoxy groups, monomer units containing hydrophobic substituents other than aromatic substituents and hydrophilic substituents containing groups that react with epoxy groups and monomer units containing hydrophobic substituents.

(3) A crosslinkable polymer comprising monomer units containing aromatic substituents and hydrophilic substituents containing groups that react with epoxy groups, monomer units containing hydrophobic substituents other than aromatic substituents and hydrophilic substituents containing epoxy groups and monomer units containing hydrophobic substituents.

In addition, monomer units containing double bonds and triple bonds, for example, vinyl groups, acetylene groups and the like for addition polymerization and preferably vinyl groups are preferred.

In addition, preferred crosslinkable polymers are the polymers obtained using a polymerization reaction of starting material monomers composed mainly of a styrene monomer and at least one or preferably two vinyl monomers represented by the general formula

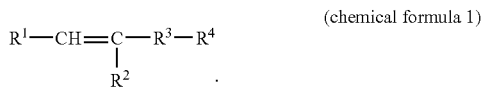
(chemical formula 1)

wherein $R^1$ represents a hydrogen atom or an alkyl group having 1 to 6 carbon atoms preferably a hydrogen atom or a methyl group, $R^2$ represents a hydrogen atom, an alkyl group having 1 to 8 carbon atoms or an aryl group containing less than 14 carbon atoms, $R^3$ represents an alkylene group having 1 to 6 carbon atoms, $—(CH_2)_n(OCH_2CHR^5)m—$, $—(CH_2)_n(OCH_2C=O)_m—$ or $—(CH_2)_n(COCH_2)_m—$, wherein $R^5$ represents a hydrogen atom or a methyl group and n and m each independently represents an integer 1 to 10, and $R^4$ represents an epoxy group, hydroxyl group, amino group, thiol group or carboxyl group.

As the vinyl monomer used as the starting material for this crosslinkable polymer, two types of monomers, a monomer of the general formula (chemical formula 1) containing an epoxy group as $R^4$ and a monomer of the general formula (chemical formula 1) containing a hydroxyl group, an amino group, a thiol group or a carboxyl group and preferably containing a hydroxyl group, are preferred.

As the styrene type monomer, styrene, α-methylstyrene, β-methylstyrene, α-ethylstyrene, o-methylstyrene, m-methylstyrene, p-methylstyrene and the like may be cited. Of these styrene and α-methylstyrene are preferred, and styrene is particularly preferred.

As the polymer containing such substituents, those containing units (monomers) shown below may be cited.

[chemical formula 2]

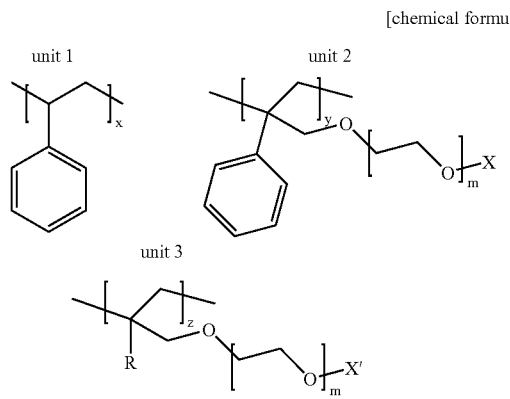

wherein m represents an integer X and X' each represent a hydroxyl group or an epoxy group and R represents an alkyl group. Unit 1 contains aromatic substituents only, Unit 2 contains both aromatic substituents and hydrophilic substituents and Unit 3 contains hydrophilic substituents. Achieving a balance between aromatic substituents and hydrophilic groups by combining these units is important. A combination of 50% by mole to 100% by mole of aromatic substituents (Unit 1+Unit 2 in this example) and 1% by mole to 50% by mole of hydrophilic substituents (Unit 2+Unit 3 in this example) is preferred.

The vinyl monomers corresponding to Units 2 and 3 can be obtained through an etherification reaction of individual allyl halides shown below and, for example, poly(ethylene glycol) and a subsequent etherification reaction of, for example, epichlorohydrin and the like with a halogenated epoxy compound.

[Chemical formula 3]

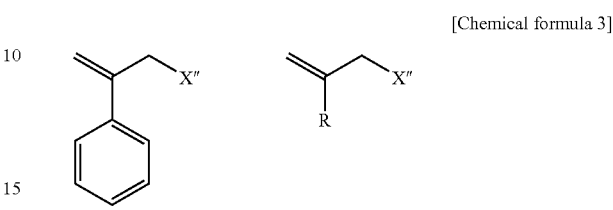

wherein X" represents a halogen atom and R represents an alkyl group.

A Lewis acid metal-incarcerated polymer micelle can be formed by adding a suitable bad solvent to a solution obtained by dissolving or dispersing such a crosslinkable polymer and a Lewis acid metal in a good solvent.

A Lewis acid metal is thought to be stabilized in such a micelle by interaction with the aromatic rings in the polymer and hetero atoms such as oxygen and the like.

THF, dioxane, acetone, DMF, NMP and the like may be used as a good polar solvent, and toluene, cyclohexane, dichloromethane, chloroform and the like may be used as a good non-polar solvent. Methanol, ethanol, butanol, amyl alcohol and the like may be used as a poor polar solvent, and hexane, heptane, octane and the like may be used as a poor non-polar solvent.

The crosslinkable polymer concentration in a good solvent varies depending on the solvent, but about 1 g/L to 100 g/L is used. In the case of a Lewis acid metal, about 1 mmole/L to 100 mmoles/L is used. In addition, the relative amounts of the bad solvent to the good solvent is ordinarily from 0.1 to ten (v/v), but from about 0.5 to five (v/v) is preferred.

The formation of such a micelle can readily be confirmed using a microscope and the like.

A micelle incarcerating a Lewis acid metal in the manner described can be crosslinked using crosslinking groups. The crosslinking stabilizes the micelle.

The crosslinking reaction can be implemented using heat or ultraviolet light irradiation depending on the crosslinkable substituent. In addition to these methods, the crosslinking reaction may be conducted according to previously well known methods used for crosslinking linear organic polymer compounds, for example, a method in which a crosslinking agent is used, a method in which a condensation agent is used, a method in which a radical polymerization catalyst such as a peroxide, an azo compound or the like is used, a method in which an acid or a base is added and heated, a method in which a dehydration condensation agent such as a carbodiimide, for example, and a suitable crosslinking agent are combined for a reaction and the like.

The temperature at which crosslinking groups are crosslinked depends on the degree of acidity of the Lewis acid used, but the crosslinking sometimes proceeds at about room temperature. For example, the temperature used is ordinarily from 50° C. to 160° C. when epoxy groups are the crosslinking groups and hydroxyl groups are the groups reacting with the epoxy groups, but from 60° C. to 140° C. is preferred and from 80° C. to 120° C. is more preferred.

The reaction time over which the heated crosslinking reaction is allowed to occur is ordinarily 0.1 hour to one hundred hours, but from one to fifty hours is preferred and two to ten hours is more preferred.

As the crosslinking agent when a crosslinking agent is used, a crosslinking agent such as, for example, a polyamine compound such as hexamethylene diamine, hexamethylene tetramine and the like, a polyol such as ethylene glycol, propylene glycol, glycerin and the like, or a polycarboxylic acid or its anhydride such as malonic acid, succinic acid, glutaric acid, adipic acid, pimelic acid, maleic acid, fumaric acid and the like, may be cited for a polymer containing epoxy groups as crosslinking groups; a crosslinking agent such as, for example, a polyhydroxy compound such as ethylene glycol, glycerin and the like or an alkylene oxide compound such as ethylene oxide, propylene oxide and the like may be cited for a polymer containing carboxyl groups as crosslinking groups; a crosslinking agent such as, for example, a polycarboxylic acid or its anhydride such as malonic acid, succinic acid, glutaric acid, adipic acid, pimelic acid, maleic acid, fumaric acid and the like, an alkylene oxide compound such as ethylene oxide, propylene oxide and the like, and a polyamine compound such as hexamethylene diamine, hexamethylene tetramine and the like may be cited for a polymer containing hydroxyl groups as crosslinking groups; and a crosslinking agent such as, for example, a polycarboxylic acid or its anhydride such as malonic acid, succinic acid, glutaric acid, adipic acid, pimelic acid, maleic acid, fumaric acid and the like or an alkylene oxide compound such as ethylene oxide, propylene oxide and the like may be cited for a polymer containing amino groups as crosslinking groups.

Dehydration condensation agents such as dicyclohexyl carbodiimide and the like may be cited, for example, as the condensation agent used when crosslinking is allowed to occur using a condensation agent for a polymer containing carboxyl groups, amino groups or hydroxyl groups as the crosslinking functional group.

The amount of a crosslinking agent used is influenced by the reactivity of the crosslinking reaction, the polymer molecular weight, the reaction conditions and the like, but from 0.1 to ten equivalents of the reactive functional groups (two groups when a difunctional crosslinking agent is used) of a crosslinking agent is ordinarily added per crosslinking group.

From 0.5 to two equivalents is preferred, and from 0.8 to 1.2 equivalents is more preferred.

The amount of crosslinking agent added may be increased or decreased according to the properties expected (for example, flexibility, swelling and the like) in the desired crosslinking type polymer catalyst.

The amount of a condensation agent is influenced by the reactivity of the crosslinking reaction, the polymer molecular weight, reaction conditions and the like, but from 0.1 to twenty equivalents of a condensation agent is ordinarily added per crosslinking group. From 0.5 to ten equivalent is preferred, and from one to three equivalents is more preferred. The amount of condensation agent added may be increased or decreased according to the properties expected (for example, flexibility, swelling and the like) in the desired crosslinking type polymer catalyst.

As a preferred form, a micelle may be used in the form of masses or films containing three dimensional network structures or as a micelle immobilized on a carrier. As the carrier, a variety of carriers such as glass, silica gel, resin and the like may be used. A polymer micelle containing metal can be strongly fixed on a carrier through crosslinking functional groups (for example, hydroxyl groups, amino groups and the like) present on a carrier surface.

A polymer micelle containing a crosslinking type metal obtained in the manner described above contains many cavities. In addition, the incarcerated Lewis acid metal exhibits excellent activity toward various reactions. This crosslinking type polymer micelle can be used in aldol reactions as well as cyanolation reactions, allylation reactions, Michael reactions, Mannich reactions, Diels Alder reactions, Friedel Craft reactions and the like known to be activated by the Lewis acid metal used here. A very high activity is displayed particularly when scandium or copper is used as the metal.

The present invention is explained in the examples shown below, but the intent of the examples is not to restrict the present invention. Various properties were measured using the devices described below. NMR Spectrum: JEOL-LA300, JEOL-LA400 OR JEOL-L1500 [manufactured by Nippon Denshi K.K.], IR Spectrum: JASCO FT/IR-610 [Nippon Bunko K.K.].

PRODUCTION EXAMPLE 1

A mixture of 2-phenylpropene (22.4 g, 190 mmoles), N-bromosuccinimide (23.7 g, 133 mmoles) and bromobenzene (76 ml) was heated in a 160° C. oil bath until the N-bromosuccinimide dissolved. The reaction mixture was allowed to cool to room temperature. The precipitate was subsequently removed using filtration and was washed using chloroform. The filtrate was distilled under reduced pressure to purify it (b.p. 80° C. to 85° C./3 mmHg), and 3-bromo-2-phenylpropene (12.1 g) was obtained. $^1$H NMR (CDCl$_3$) δ =4.39 (s, 2H), 5.49 (s, 1H), 5.56 (s, 1H), 7.33-7.51 (m, 5H); $^{13}$C NMR (CDCl$_3$) δ=34.2, 117.2, 126.1, 128.3, 128.5, 137.6, 144.2.

A DMF solution (5 ml) of glycidol (7.4 g, 100 mmoles) was added to a DMF suspension (75 ml) of 60% sodium hydride (1.6 g, 40 mmoles) at 0° C. Next, a DMF solution (10 ml) of the 3-bromo-2-phenylpropene (3.94 g, 20 mmoles) obtained as described above was added at the same temperature. The mixture was subsequently agitated at room temperature for twenty-four hours. The reaction mixture was cooled to 0° C. and diluted using diethyl ether. A saturated aqueous ammonium chloride solution was subsequently added to terminate the reaction. The aqueous layer was extracted several times using diethyl ether, and the organic layer was combined and dried using anhydrous sodium sulfate. Upon filtration, the solvent was concentrated, and the residue was purified using silica gel column chromatography (hexane-AcOEt) to obtain 2-[2-phenyl allyloxy] methyl] oxylan (2.66 g, 70%). $^1$H NMR (CDCl$_3$) 67 =2.59 (dd, 1H, J=2.7, 5.1 Hz), 2.78 (dd, 1H, J=4.2, 5.1 Hz), 3.13-3.17 (m, 1H), 3.46 (dd, 1H, J=5.8, 11.5 Hz), 3.77 (dd, 1H, J=3.2, 11.5 Hz), 4.41 (ddd, 1H, J=0.7, 1.2, 12.9 Hz), 4.48 (ddd, 1H, J=0.5, 1.2, 12.9 Hz), 5.34-5.36 (m, 1H), 5.53-5.54 (m, 1H), 7.45-7.48 (m, 5H); $^{13}$C NMR (CDCl$_3$) δ=44.3, 50.8, 70.5, 73.2, 114.6, 126.0, 127.8, 128.4, 138.6, 143.9; IR (KBr) 3000, 2924, 2867, 1911, 1812, 1701, 1630, 1512, 1479, 1407, 1337, 1254, 1205, 1107, 991, 909, 839 cm$^{-1}$; HRMS (EI): Calcd for C$_{13}$H$_{16}$O$_2$(M+) 190.0994, found 190.0998.

Styrene (12.5 g, 120 mmoles), the 2-[(2-phenyl allyloxy) methyl] joxylan obtained as described above (2.85 g, 15 mmoles), tetraethyleneglycol mono-2-phenyl-2-propenyl ether (4.66 g, 15 mmoles) and AIBN (172.4 mg, 1.05 mmoles) were dissolved in chloroform (19 ml), and the solution was heated and agitated for forty-eight hours in argon atmosphere under reflux conditions. Upon cooling, the reaction mixture was poured into methanol (MeOH) (600 ml) and the polymer solidified. The supernatant solution was removed by decantation, the solids were dissolved in a small amount of tetrahydrofuran, and the solution was poured into methanol again. The precipitated polymer was filtered, dried at room temperature under reduced pressure and 12.0 g of a polymer was obtained (yield 60%).

The polymer obtained had the structure shown below. The composition ratio of individual monomer units was (x/y/z)=91/5/4, weight average molecular weight (Mw)=31,912, number average molecular weight (Mn)=19,468 and degree of dispersion (Mw/Mn)=1.64. The polymer formed is shown below as Polymer (1).

[Chemical formula 4]

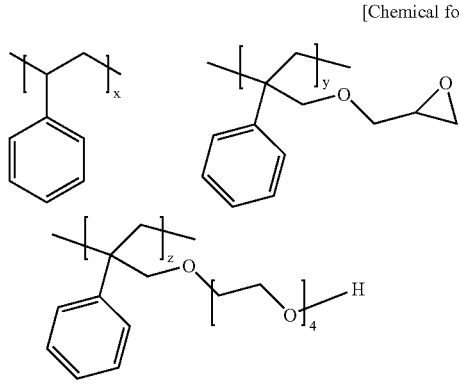

EXAMPLE 1

Scandium triflate (200 mg, 0.406 mmole) was added at room temperature to a toluene solution (40 ml) obtained by dissolving Polymer (1) (2.0 g), and the solution was agitated for fifteen minutes. Hexane (160 ml) was added dropwise to this solution and was agitated for an additional thirty minutes at room temperature to conduct a coacervation. The polymer that separated out was filtered, washed using hexane and subsequently dried under reduced pressure at room temperature. This polymer was treated for two hours at 120° C. to conduct a crosslinking reaction and was washed using toluene and dichloromethane. The polymer was subsequently dried under reduced pressure for two hours at 100° C. to obtain white solids composed of scandium triflate immobilized on a polymer 2.1 g, 0.195 mmole/g). The scandium triflate loading amount was calculated using the value obtained by quantitatively measuring the amount of scandium flowing out into all of the solvent used during the synthesis using a fluorescence X-ray device.

EXAMPLE 2

A dichloromethane solution (1.5 ml) of benzaldehyde (42 mg, 0.40 mmole) was added at room temperature to the polymer-immobilized scandium triflate (103 mg, 0.020 mmole) obtained in Example 1. Next a dichloromethane solution (1.0 ml) of ketene silyl acetal derived from methyl isobutyrate was added dropwise over three hours. After the reaction, hexane (5 ml) was added, filtered and a polymer-immobilized catalyst was recovered after washing it using dichloromethane. The filtrate and the wash solution were concentrated, and 1 normal hydrochloric acid/THF solution (1/20, 5 ml) was added to the residue obtained while cooling the reaction mixture using ice. The mixture was agitated for an hour. The residue obtained upon removing the solvent using distillation was purified using silica gel thin layer chromatography (ethyl acetate/hexane=1/4), and the desired aldol adduct was obtained in the form of white solids (69 mg, 83%). The polymer-immobilized catalyst was recovered and was recycled. The yields of the desired material were as described below. The yield after the second cycle was (83%), after the third cycle was (84%), after the fourth cycle was (83%) and after the fifth cycle was (81%).

$^1$H-NMR(CDCl$_3$): δ 1.11 (s, 3H), 1.14 (s, 3H), 3.09 (br, 1H), 3.72 (s, 3H), 4.89 (br, 1H) 7.24 7.33 (m, 5H) $^{13}$C-NMR (CDCl$_3$): δ 19.0, 23.0, 47.7, 52.1, 78.7, 127.7, 127.8, 140.0, 178.2

EXAMPLE 3

Polymer (1) (0.5 g) was dissolved in dichloromethane (10 ml), copper trifluoromethane sulfonate (36 mg) was added and the solution was agitated for twelve hours at room temperature. Next, hexane that is a bad solvent for the polymer solution was slowly added, and the polymer solidified. The solvent was removed, and the mixture was agitated for two hours at 120° C. in the absence of a solvent. The polymer was cooled to room temperature, dichloromethane was subsequently added, and the mixture was agitated for a while. Dichloromethane was subsequently used to conduct filtration and washing, and the solids were dried under reduced pressure. A crosslinking type micro-incarcerated copper catalyst [PI Cu (OTf)$_2$, 419 mg] was obtained. The copper metal introduction rate was quantitatively determined using a fluorescence X ray analysis device by adding concentrated sulfuric acid to PI Cu(OTf)$_2$, agitating the mixture for an hour at 180° C., adding concentrated nitric acid, further agitating the mixture for four hours, cooling and diluting the product with distilled water.

EXAMPLE 4

Benzaldehyde (0.03 ml, 0.3 mmole) and ketene silyl acetal (80 mg, 0.45 mmole) derived from methyl isobutyrate were mixed in dichloromethane (2 ml) in the presence of the crosslinking type micro-incarcerated copper catalyst (0.03 mmole) obtained in Example 3. The mixture was agitated for two days at room temperature. The mixture was filtered after diluting, and the catalyst was washed using dichloromethane. The filtrate was concentrated, and the copper elution from the catalyst was measured using fluorescence X ray analysis. After the measurement, the mixture was poured into 1 N aqueous hydrochloric acid solution and was extracted twice using chloroform. The organic layer was washed using distilled water and saturated aqueous sodium chloride solution and dried to concentrate it. The material was purified using silica gel thin layer chromatography, and a desired aldol adduct (38 mg, 61%) was obtained in the form of white solids.

The PI Cu(OTf)$_2$ was recovered, dried for three hours under reduced pressure and recycled.

EXAMPLE 5

The same experiment was conducted using a variety of silicon enolates in place of the ketene silyl acetal from Example 2. The reaction is shown below, and the results are shown in Table 1.

[Chemical Equation 5]

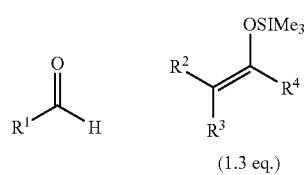

TABLE 1

| entry | R¹ | R² | R³ | R⁴ | yield (%) |
|---|---|---|---|---|---|
| 1 | phenyl | Me | Me | OMe | 83 |
| 2 | 4-Me-phenyl | Me | Me | OMe | 90 |
| 3 | 2-Me-phenyl | Me | Me | OMe | 93 |
| 4 | 4-Cl-phenyl | Me | Me | OMe | 93 |
| 5 | PhCH₂CH₂ | Me | Me | OMe | 70 |
| 6 | 2-furyl | Me | Me | OMe | 75 |
| 7 | 2-thienyl | Me | Me | OMe | 93 |
| 8 | 2-pyridyl | Me | Me | OMe | 85 |
| 9 | phenyl | H | Me | SEt | 80 (35/65)[a] |
| 10 | phenyl | H | H | SEt | 83 |
| 11 | phenyl | Me | H | Et | 75 (48/52)[a] |
| 12 | phenyl | H | —(CH₂)₄— | | 65 (42/58)[a] |
| 13 | phenyl | Me | H | Ph | 70 (58/42)[a] |
| 14 | phenyl | Me | H | Ph | 32 |
| 15 | phenyl | Me | H | Ph | 65 |

[a] syn/anti

EXAMPLE 6

The same reaction described in Example 1 was conducted using THF-hexane (1/3) in place of the toluene used in Example 1, and polymer-immobilized scandium triflate [PMI Sc(OTf)₃] was obtained in the form of white solids (2.1 g, 0.186 mmole/g).

EXAMPLE 7

The PMI Sc(OTf)₃ obtained in Example 6 was used to conduct the same reaction described in Example 2, and a desired aldol adduct was obtained (76 mg, 92%). The PMI Sc(OTf)3 was recovered and used to conduct the same experiment, and the same product was obtained (76 mg, 92%). In both cases, the Sc leakage during the reaction and the after treatment was less than the detection limit (0.05%) of the ICP analysis. The reaction equation is shown below.

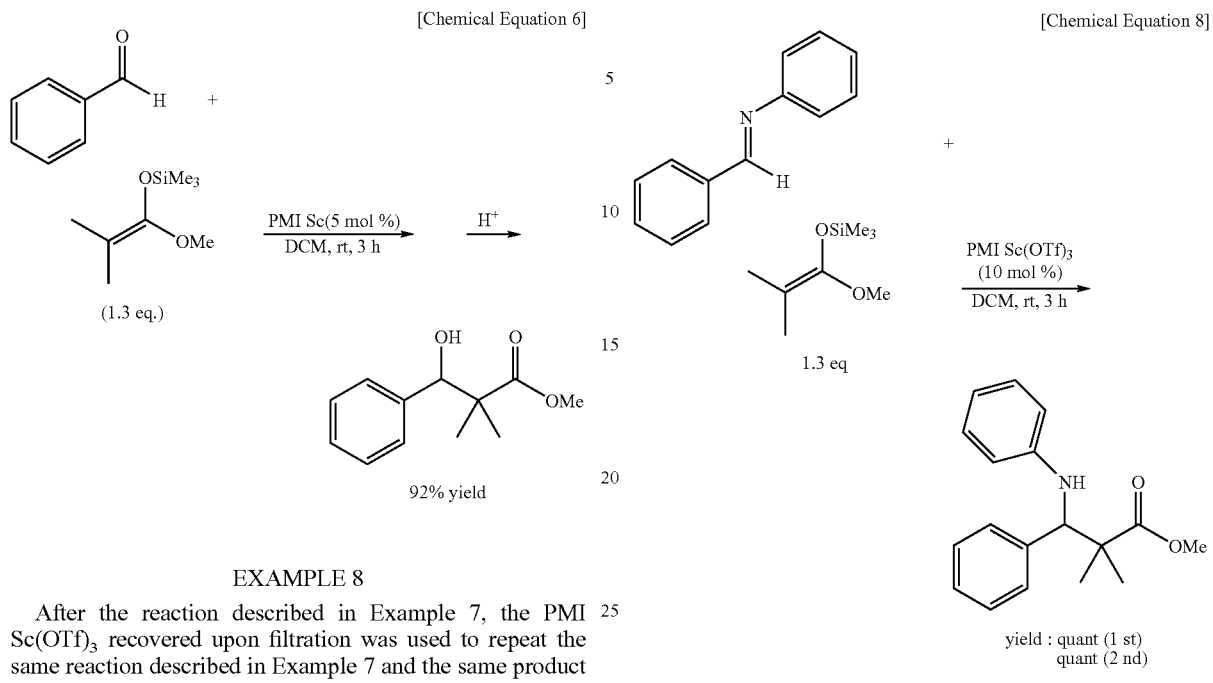

[Chemical Equation 6]

EXAMPLE 8

After the reaction described in Example 7, the PMI Sc(OTf)$_3$ recovered upon filtration was used to repeat the same reaction described in Example 7 and the same product was obtained (76 mg, 92%). In both cases, the Sc leakage during the reaction and the after treatment was less than the detection limit (0.05%) of the ICP analysis.

EXAMPLE 9

A Mannich type reaction was conducted using the same conditions described in Example 7 using N-benzylidene aniline in place of benzaldehyde, and 113 mg (96%) of the desired adduct was obtained. The Sc leakage during the reaction and the after treatment was less than the detection limit (0.05%) of the ICP analysis. The reaction equation is shown by the equation below.

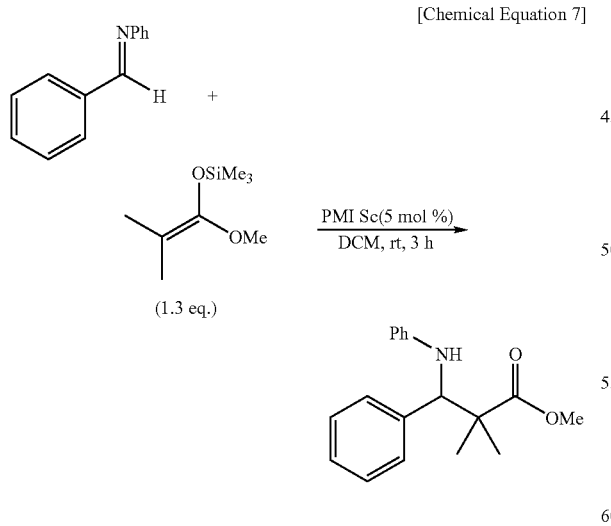

[Chemical Equation 7]

The reaction described in Example 9 was conducted using 10% by mole of PMI Sc(OTf)$_3$, and the desired product was obtained quantitatively. Furthermore, the PMI Sc(OTf)$_3$ recovered upon filtration after the reaction was used to repeat the same reaction. The desired product was obtained quantitatively again. The reaction equation is shown by the equation below.

[Chemical Equation 8]

EXAMPLE 11

The PMI Sc(OTf)$_3$ obtained in Example 6 was used to conduct a Michael reaction using methyl 2,3-dihydro-1-oxo-1H-indene-2-carboxylate and but-3-en-2-one (two equivalents). The same procedure described in Example 2 was used but with changes in the amount of catalyst, solvent and reaction time used. In all cases, the desired adduct was obtained in high yields, and no reduction in the yield was observed when a recovered catalyst was used. The reaction equation and the results are shown in the table below.

TABLE 2

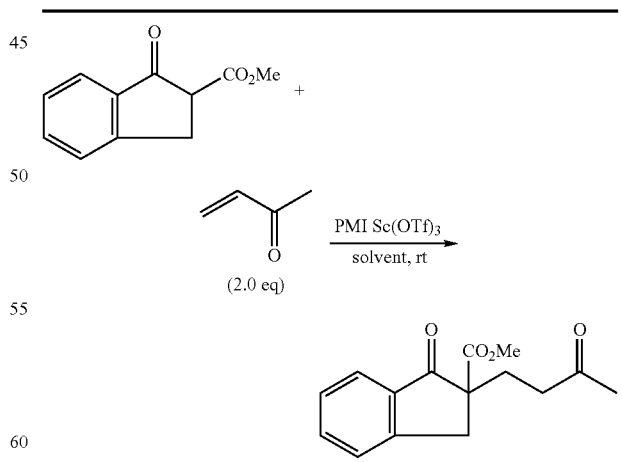

| entry | PMI SC(OTf)$_3$ (mol %) | solvent | time (h) | yield (%) 1st | 2nd | 3rd |
|---|---|---|---|---|---|---|
| 1 | 10 | MeCN | 2 | 96 | 95 | 95 |
| 2 | 5 | MeCN | 4 | 92 | 94 | 92 |

TABLE 2-continued

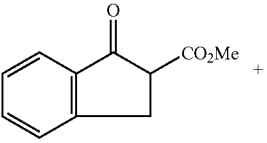

| | PMI SC(OTf)₃ | | time | yield (%) | | |
|---|---|---|---|---|---|---|
| entry | (mol %) | solvent | (h) | 1st | 2nd | 3rd |
| 3 | 10 | toluene | 4 | quant | 96 | 98 |
| 4 | 10 | DCM | 12 | 92 | 92 | 91 |

EXAMPLE 12

The Michael reaction described in Example 11 was conducted using various substrates and the conditions shown in Example 2. In all cases, a desired adduct was obtained in high yield. The reaction equation and the results are shown in the table below.

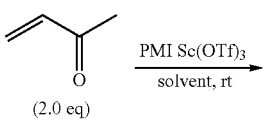

| donor | acceptor | product | h | yield(%) | dr |
|---|---|---|---|---|---|
| 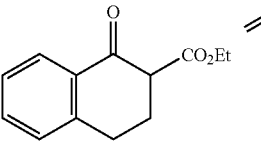 | 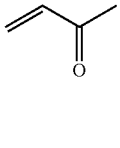 | 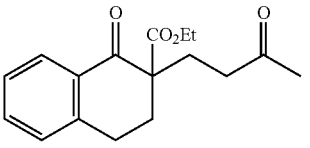 | 4 | 94 | — |
| 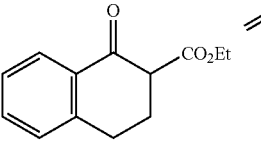 | 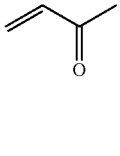 | 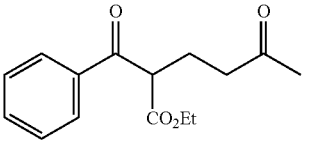 | 9 | 92 | — |
| 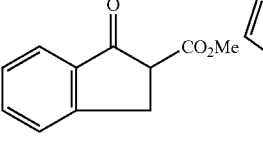 | 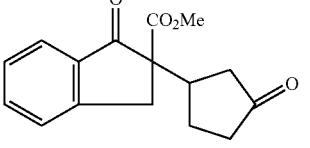 | 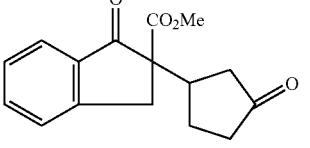 | 6 | 96 | 66/34 |

What is claimed is:

1. A polymer incarcerated Lewis acid metal catalyst comprising a Lewis acid metal incarcerated in a crosslinked polymer, wherein the crosslinked polymer is obtained by crosslinking a crosslinkable polymer which has hydrophilic substituents containing crosslinking groups linked directly to the crosslinkable polymer main chain and hydrophobic substituents linked directly to the crosslinkable polymer main chain, wherein the hydrophobic substituents do not contain hydrophilic groups or crosslinking groups, and further wherein the crosslinkable polymer contains at least one type of monomer unit containing (a) an aromatic hydrophobic substituent which does not contain hydrophilic groups or crosslinking groups and (b) a hydrophilic substituent containing a crosslinking group.

2. The catalyst of claim 1, wherein the crosslinkable polymer further contains at least one type of monomer unit containing a hydrophobic substituent but no hydrophilic substituent containing a crosslinking group.

3. The catalyst of claim 2, wherein the crosslinkable polymer further contains at least one type of a monomer unit containing a hydrophobic substituent other than an aromatic substituent and a hydrophilic substituent containing a crosslinking group but no hydrophilic substituent containing a crosslinking group.

4. The catalyst of claim 1, wherein the crosslinkable polymer contains a monomer unit containing a hydrophilic substituent containing an epoxy group and a monomer unit containing a hydrophilic substituent containing a group that reacts with the epoxy group.

5. The catalyst of claim 4, wherein the crosslinkable polymer contains a monomer unit containing an aromatic substituent and a hydrophilic substituent containing an epoxy group, a monomer unit containing an aromatic substituent and a hydrophilic substituent containing a group that reacts with the epoxy group, and a monomer unit containing a hydrophobic substituent but no hydrophilic substituent containing a crosslinking group.

6. The catalyst of claim 4, wherein the crosslinkable polymer contains a monomer unit containing an aromatic substituent and a hydrophilic substituent containing an epoxy group, a monomer unit containing a hydrophobic substituent other than an aromatic substituent and a hydrophilic substituent containing a group that reacts with the epoxy group and a monomer unit containing a hydrophobic substituent but no hydrophilic substituent containing a crosslinking group.

7. The catalyst of claim 4, wherein the crosslinkable polymer contains a monomer unit containing an aromatic substituent and a hydrophilic substituent containing a group that reacts with an epoxy group, a monomer unit containing a hydrophobic substituent other than an aromatic substituent and a hydrophilic substituent containing an epoxy group and a monomer unit containing a hydrophobic substituent but no hydrophilic substituent containing a crosslinking group.

8. The catalyst of claim 4, wherein the group that reacts with an epoxy group is at least one selected from a group comprising a hydroxyl group, an amino group, a thiol group and a carboxyl group.

9. The polymer incarcerated Lewis acid metal catalyst of claim 1, wherein the crosslinkable polymer is obtained by polymerizing, as main monomers, a styrene monomer, a vinyl monomer represented by the general formula

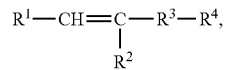

wherein $R^1$ represents a hydrogen atom or an alkyl group having 1 to 6 carbon atoms, $R^2$ represents a hydrogen atom, an alkyl group having 1 to 8 carbon atoms or an aryl group containing less than 14 carbon atoms, $R^3$ represents an alkylene group having 1 to 6 carbon atoms, $—(CH_2)_n(OCH_2CHR^5)_m—$, $—(CH_2)_n(OCH_2CO=O)_m—$ or $—(CH_2)_n(COCH_2)_m—$, wherein $R_5$ represents a hydrogen atom or a methyl group and n and m each independently represent integers 1 to 10, and $R_4$ represents an epoxy group, and a vinyl monomer represented by the general formula

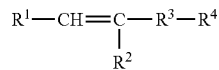

wherein $R^1$ to $R^3$ and n and m independently represent the same as above, and $R^4$ represents at least one reactive group selected from a group comprising a hydroxyl group, an amino group, a thiol group and a carboxyl group.

10. The catalyst of claim 1 prepared by mixing an organic solution containing the crosslinkable polymer and the Lewis acid metal to prepare a polymer micelle incarcerating Lewis acid metal, and crosslinking the polymer micelle incarcerating Lewis acid metal.

11. The catalyst of claim 1, wherein the Lewis acid metal is represented by $MY_n$, wherein M represents Cu, Zn, Fe, Sc or a lanthanoid element, Y represents a halogen atom, OAc, $OCOCF_3$, $ClO_4$, $SbF_6$, $PF_6$ or $OSO_2CF_3$ and n is 2 or 3.

12. An aldol, cyanolation, allylation, Michael, Mannich, Diels Alder or Friedel Craft reaction conducted in the presence of the catalyst of claim 1.

13. The catalyst of claim 2, wherein the crosslinkable polymer contains a monomer unit containing a hydrophilic substituent containing an epoxy group and a monomer unit containing a hydrophilic substituent containing a group that reacts with the epoxy group.

14. The catalyst of claim 3, wherein the crosslinkable polymer contains a monomer unit containing a hydrophilic substituent containing an epoxy group and a monomer unit containing a hydrophilic substituent containing a group that reacts with the epoxy group.

15. The catalyst of claim 9 prepared by mixing an organic solution containing the crosslinkable polymer and the Lewis acid metal to prepare a polymer micelle incarcerating Lewis acid metal, and crosslinking the polymer micelle incarcerating Lewis acid metal.

16. The catalyst of claim 9, wherein the Lewis acid metal is represented by $MY_n$, wherein M represents Cu, Zn, Fe, Sc or a lanthanoid element, Y represents a halogen atom, OAc, $OCOCF_3$, $ClO_4$, $SbF_6$, $PF_6$ or $OSO_2CF_3$ and n is 2 or 3.

17. The catalyst of claim 10, wherein the Lewis acid metal is represented by $MY_n$, wherein M represents Cu, Zn, Fe, Sc or a lanthanoid element, Y represents a halogen atom, OAc, $OCOCF_3$, $ClO_4$, $SbF_6$, $PF_6$ or $OSO_2CF_3$ and n is 2 or 3.

18. An aldol, cyanolation, allylation, Michael, Mannich, Diels Alder or Friedel Craft reaction conducted in the presence of the catalyst of claim 9.

19. An aldol, cyanolation, allylation, Michael, Mannich, Diels Alder or Friedel Craft reaction conducted in the presence of the catalyst of claim 10.

* * * * *